US009534010B2

(12) United States Patent
Hebert (10) Patent No.: US 9,534,010 B2
(45) Date of Patent: Jan. 3, 2017

(54) STABLE INDOLE-3-PROPIONATE SALTS OF S-ADENOSYL-L-METHIONINE

(71) Applicant: HEBERT SAM-E LLC, Carson City, NV (US)

(72) Inventor: Rolland F. Hebert, Seattle, WA (US)

(*) Notice: Subject to any disclaimer, the term of this patent is extended or adjusted under 35 U.S.C. 154(b) by 0 days.

(21) Appl. No.: 14/760,067

(22) PCT Filed: Jan. 16, 2014

(86) PCT No.: PCT/US2014/011935
§ 371 (c)(1),
(2) Date: Jul. 9, 2015

(87) PCT Pub. No.: WO2014/113609
PCT Pub. Date: Jul. 24, 2014

(65) Prior Publication Data
US 2015/0344517 A1    Dec. 3, 2015

Related U.S. Application Data

(60) Provisional application No. 61/753,300, filed on Jan. 16, 2013, provisional application No. 61/792,467, filed on Mar. 15, 2013.

(51) Int. Cl.

| | | |
|---|---|---|
| *A01N 43/04* | (2006.01) | |
| *A61K 31/70* | (2006.01) | |
| *C07H 19/16* | (2006.01) | |
| *C07D 209/42* | (2006.01) | |
| *C07H 19/167* | (2006.01) | |
| *A61K 31/708* | (2006.01) | |
| *A61K 31/7076* | (2006.01) | |

(52) U.S. Cl.
CPC ............. *C07H 19/16* (2013.01); *C07D 209/42* (2013.01); *C07H 19/167* (2013.01); *A61K 31/708* (2013.01); *A61K 31/7076* (2013.01)

(58) Field of Classification Search
None
See application file for complete search history.

(56) References Cited

U.S. PATENT DOCUMENTS

| | | |
|---|---|---|
| 2,969,353 A | 1/1961 | Shunk et al. |
| 3,707,536 A | 12/1972 | Haid et al. |
| 3,893,999 A | 7/1975 | Fiecchi |
| 3,954,726 A | 5/1976 | Fiecchi |
| 4,028,183 A | 6/1977 | Fiecchi |
| 4,057,686 A | 11/1977 | Fiecchi |
| 4,109,079 A | 8/1978 | Kawahara et al. |
| 4,242,505 A | 12/1980 | Kawahara et al. |
| 4,369,177 A | 1/1983 | Kozaki et al. |
| 4,465,672 A | 8/1984 | Gennari |
| 4,543,408 A | 9/1985 | Gennari |
| 4,558,122 A | 12/1985 | Gennari |
| 4,764,603 A | 8/1988 | Zappia et al. |
| 4,990,606 A | 2/1991 | Gennari |
| 5,073,546 A | 12/1991 | Zappia et al. |
| 5,102,791 A | 4/1992 | Gennari |
| 5,114,931 A | 5/1992 | Gennari |
| 5,128,249 A | 7/1992 | Gennari |
| 5,166,328 A | 11/1992 | Kurobe et al. |
| 6,117,849 A | 9/2000 | Zimmermann et al. |
| 2002/0173012 A1 | 11/2002 | Berna et al. |
| 2002/0188116 A1 | 12/2002 | Deshpande et al. |
| 2003/0032796 A1 | 2/2003 | Deshpande et al. |
| 2006/0127506 A1 | 6/2006 | Hebert |
| 2010/0004191 A1 | 1/2010 | Hebert |

FOREIGN PATENT DOCUMENTS

| | | |
|---|---|---|
| WO | WO 02/092105 A1 | 11/2002 |
| WO | 2007/004244 A1 | 1/2007 |

OTHER PUBLICATIONS

Bottiglieri et al., "Cerebrospinal fluid S-adenosylmethionine in depression and dementia: effects of treatment with parenteral and oral S-adenosylmethionine," *Journal of Neurology, Neurosurgery, and Psychiatry* 53: 1096-1098, 1990.
Bottiglieri et al., "The Clinical Potential of Ademetionine (*S*-Adenosylmethionine) in Neurological Disorders," *Drugs* 48(2): 137-152, 1994.
Bottiglieri, "Isocratic High Performance Liquid Chromatographic Analysis of S-Adenosylmethionine and S-Adenosylhomocysteine in Animal Tissues: the Effect of Exposure to Nitrous Oxide," *Biomedical Chromatography* 4(6): 239-241, 1990.
Cheng et al., "Levels of L-Methionine *S*-Adenosyltranferase Activity in Erythrocytes and Concentrations of *S*-Adenosylmethionine and *S*-Adenosylhomocysteine in Whole Blood of Patients with Parkinson's Disease," *Experimental Neurology* 145: 580-585, 1997.
Di Padova, "S-Adenosylmethionine in the Treatment of Osteoarthritis," *The American Journal of Medicine* 83(suppl 5A): 60-65, Nov. 20, 1987.
Evidence Report No. 64, U.S. Department of Health and Human Services, Public Health Service, Agency for Healthcare Research and Quality, Aug. 2002.
Friedel et al., "*S*-Adenosyl-L-Methionine: A Review of its Pharmacological Properties and Therapeutic Potential in Liver Dysfunction and Affective Disorders in Relation to its Physiological Role in Cell Metabolism," *Drugs* 38(3): 389-416, 1989.
Gross et al., "Enzymatic Synthesis of *S*-Adenosyl-L-Methionine from L-Methionine and ATP," *Applied Biochemistry and Biotechnology* 8: 415-422, 1983, 8 pages.
Kagan et al., "Oral *S*-Adenosylmethionine in Depression: A Randomized, Double-Blind, Placebo-Controlled Trial," *Am. J. Psychiatry* 147(5): 591-595, May 1990.
Mato et al., "S-Adenosylmethionine in alcoholic liver cirrhosis: a randomized, placebo-controlled, double-blind, multicenter clinical trial," *Journal of Hepatology* 30: 1081-1089, 1999.

(Continued)

*Primary Examiner* — Patrick Lewis (57) ABSTRACT

Stable indole-3-propionic acid salts of S-adenosyl-L-methionine, or a pharmaceutically acceptable salt thereof, are disclosed, as well as pharmaceutical compositions comprising the indole-3-propionic acid salts, methods of using the indole-3-propionic acid salts and processes for making same.

10 Claims, 6 Drawing Sheets

(56) References Cited

OTHER PUBLICATIONS

Matos et al., "S-Adenosylmethionine: Studies on Chemical and Enzymatic Synthesis," *Biotechnology and Applied Biochemistry* 9: 39-52, 1987.

Morrison et al., "Brain S-Adenosylmethionine Levels Are Severely Decreased in Alzheimer's Disease," *J. Neurochem.* 67(3): 1328-1331, 1996.

Stewart et al., "Comparison of Intestinal Permeabilities Determined in Multiple in Vitro and in Situ Models: Relationship to Absorption in Humans," *Pharmaceutical Research* 12(5): 693-699, 1995.

Tavoni et al., "Evaluation of S-Adenosylmethionine in Primary Fibromyalgia: A Double-Blind Crossover Study," *The American Journal of Medicine* 83(suppl 5A): 107-110, Nov. 20, 1987.

Vendemiale et al., "Effects of Oral S-Adenosyl-L-Methionine on Hepatic Glutathione in Patients with Liver Disease," *Scand. J. Gastroenterol* 24: 407-415, 1989.

STABLE INDOLE-3-PROPIONATE SALTS OF S-ADENOSYL-L-METHIONINE

FIELD OF THE INVENTION

The present invention relates to stable indole-3-propionate salts of S-adenosyl-L-methionine, or a pharmaceutically acceptable salt thereof, processes for preparing the indole-3-propionate salts, pharmaceutical compositions comprising the indole-3-propionate salts, and therapeutic uses thereof. These indole-3-propionate salts possess potent activity in treating various conditions associated with aging and other conditions in mammals.

BACKGROUND OF THE INVENTION

S-Adenosyl-L-methionine (SAMe)

S-adenosyl-L-methionine (SAMe) is a naturally occurring substance that is present in all living organisms and has a number of very important biological functions. SAMe exists in two important diasteriomeric forms as (S,S)S-adenosyl-L-methionine and (R,S)S-adenosyl-L-methionine. Among these functions are the following: methyl group donor in transmethylation reactions (it is the sole methyl group donor in such reactions-including methylation of DNA, proteins, hormones, catechol and indoleamines and phosphatidylethanolamine to phosphatidylcholine); a substrate of an enzyme lyase that converts SAMe to the molecule methylthioadenosine and homoserine; an aminobutyric chain donor to tRNA; and an aminoacidic chain donor in the biosynthesis of biotin. SAMe, after decarboxylation, is also the donor of aminopropyl groups for the biosynthesis of neuroregulatory polyamines spermidine and spermine. (Zappia et al. (1979), "Biomedical and Pharmacological roles of Adenosylmethionine and the Central Nervous System", page 1, Pergamon Press. NY). SAMe has been used clinically for more than twenty years in the treatment of liver disease (Friedel H, Goa, K. L., and Benfield P. (1989), "S-Adenosyl-1-methionine: a review of its pharmacological properties and therapeutic potential in liver dysfunction and affective disorders in relation to its physiological role in cell metabolism", *Drugs*, 38, 389-416), arthritis (Di Padova C, (1987), "SAMe in the treatment of osteoarthritis: review of the clinical studies", *Am J. Med.* 83, (Suppl. 5), 6-65), and depression (Kagan, B, Sultzer D. L., Rosenlicht N and Gerner R. (1990), "Oral S-adenosylmethionine in depression: a randomized, double-blind, placebo-controlled trial", *Am. J. Psychiatry* 147, 591-595). Alzheimer's patients have reduced cerebral spinal fluid levels of SAMe (Bottiglieri et al, (1990), "Cerebrospinal fluid SAMe in depression and dementia: effects of treatment with parenteral and oral S-adenosyl-1-methionine", *J. Neurol. Neurosurg. Psychiatry* 53, 1096-1098). In a preliminary study, SAMe was able to produce cognitive improvement in patients with Alzheimer's disease (Bottiglieri et al. (1994), "The clinical potential of admetionine (S-adenosyl-1-methionine) in neurological disorders", *Drugs* 48, 137-152).

SAMe brain levels in patients with Alzheimer's disease are also severely decreased (Morrison et al., (1996), "Brain S-adenosylmethionine levels are severely decreased in Alzheimer's disease", *Journal of Neurochemistry*, 67, 1328-1331. Patients with Parkinson's disease have also been shown to have significantly decreased blood levels of SAMe. (Cheng et al., (1997), "Levels of L-methionine S-adenosyltransferase activity in erythrocytes and concentrations of S-adenosylmethionine and S-adenosylhomocysteine in whole blood of patients with Parkinson's disease", *Experimental Neurology* 145, 580-585). Oral SAMe administration to patients with and without liver disease has resulted in increases in liver glutathione levels (Vendemiale G et al., "Effect of oral SAMe on hepatic glutathione in patients with liver disease", *Scand J Gastroenterol* 1989;24:407-15.

Oral administration of SAMe to patients suffering from intrahepatic cholestasis had improvements in both the pruritus as well as the biochemical markers of cholestasis (Giudici et al., "The use of admetionine (SAMe) in the treatment of cholestatic liver disorders", *Meta-analysis of clinical trials*, Mato et al. editors, Methionine Metabolism: Molecular Mechanism and Clinical Implications. Madrid: CSIC Press; 1992 pp 67-79). Oral SAMe administration to patients suffering from primary fibromyalgia resulted in significant improvement after a short-term trial (Tavoni et al., "Evaluation of S-adenosylmethionine in Primary Fibromyalgia", *The American Journal of Medicine*, Vol 83 (suppl 5A), pp 107-110, 1987). Lee Hong Kyu disclosed in a PCT published patent application No. WO 02/092105 (Nov. 21, 2002) that SAMe could be used to treat diabetes and insulin resistance.

A recently published evidence report entitled "SAMe for the treatment of depression, osteoarthritis and liver disease" provides both safety and clinical efficacy data for SAMe (Evidence Report number 64, US Department of Health and Human Services, Public Health Service, Agency for Healthcare Research and Quality. October 2002).

SAMe is clinically useful in many apparently unrelated areas because of its important function in basic metabolic processes. One of its most striking clinical uses is in the treatment of alcoholic liver cirrhosis that, until now, remained medically untreatable. The ability of oral SAMe in alcoholic liver cirrhosis in decreasing the overall mortality and/or progression to liver transplant by 29% vs 12% as compared with a placebo treated group has been demonstrated (Mato et al. (1999), "S-adenosylmethionine in alcohol liver cirrhosis: a randomized, placebo-controlled, double blind, multi-center clinical trial", *Journal of Hepatology*, 30, 1081-1089). The extensive clinical use of SAMe has proven its efficacy as well as its absence of toxicity in a number of different clinical conditions.

SAMe presents certain difficult problems in terms of its stability at ambient temperature that result in degradation of the molecule to undesirable degradation products such as methylthioadenosine. In addition, the majority of the salts used to stabilize SAMe are sulfur based and these sulfur based salts are the most likely cause of the gastrointestinal discomfort that patients report as a reason for discontinuing treatment.

SAMe has been the subject of numerous patents directed both towards obtaining stable salts of SAMe and towards the provision of preparation processes which can be implemented on an industrial scale. There exist numerous patents disclosing salts of SAMe but none discloses indole-3-propionic acid (IPA) salts of SAMe. U.S. Pat. No. 3,893,999 discloses a new salt of SAMe made with tri-p-toluensulphonate but not the use of indole-3-propionic acid in forming a stable salt of SAMe, or a pharmaceutically acceptable salt thereof. U.S. Pat. No. 3,954,726 discloses double salts of SAMe but does not disclose the use of indole-3-propionic acid in forming a stable salt of SAMe, or a pharmaceutically acceptable salt thereof. U.S. Pat. No. 4,028,183 discloses, inter alia, p-toluene sulfonate as a means to stabilize the SAMe molecule but does not disclose the use of indole-3-propionic acid in forming a stable salt of SAMe, or a pharmaceutically acceptable salt thereof. U.S. Pat. No. 4,057,686 discloses stable salts of SAMe but does not disclose the use of indole-3-propionic acid in forming stable salts of SAMe, or a pharmaceutically acceptable salt thereof. U.S. Pat. No. 4,465,672 discloses new SAMe salts but does not disclose the use of indole-3-propionic acid in forming stable salts of SAMe, or a pharmaceutically acceptable salt thereof. U.S. Pat. No. 4,543,408 discloses new SAMe salts but does not disclose the use of indole-3-propionic acid in forming stable salts of SAMe, or a pharmaceutically acceptable salt thereof. U.S. Pat. No. 4,558,122 discloses new SAMe salts but does not disclose the use of indole-3-propionic acid in forming stable salts of SAMe, or a pharmaceutically acceptable salt thereof. U.S. Pat. No. 4,990,606 discloses new salts of SAMe but does not disclose the use of indole-3-propionic acid in forming stable salts of SAMe.

In addition, U.S. Pat. No. 5,102,791 discloses, inter alia, a 1,4 butanedisulfonate salt of SAMe but not the use of indole-3-propionic acid in forming a stable salt of SAMe, or a pharmaceutically acceptable salt thereof. U.S. Pat. No. 5,114,931 discloses injectable SAMe salts but does not disclose the use of indole-3-propionic acid in forming stable salts of SAMe, or a pharmaceutically acceptable salt thereof. U.S. Pat. No. 5,128,249 discloses new SAMe salts but does not disclose the use of indole-3-propionic acid in forming stable salts of SAMe. U.S. Pat. No. 3,707,536 discloses a new SAMe bisulfate salt but not the use of indole-3-propionic acid in forming a stable salt of SAMe, or a pharmaceutically acceptable salt thereof. U.S. Pat. No. 4,109,079 discloses new stable SAMe salts but does not disclose the use of indole-3-propionic acid in forming stable salts of SAMe, or a pharmaceutically acceptable salt thereof. U.S. Pat. No. 4,242,505 discloses new stabilizing salts of SAMe but does not disclose the use of indole-3-propionic acid in forming stable salts of SAMe. U.S. Pat. No. 4,369,177 discloses stable compositions of SAMe and SAMe salts using a salt of a bivalent or trivalent metal but does not disclose the use of indole-3-propionic acid salts in forming stable salts off SAMe, or a pharmaceutically acceptable salt thereof. U.S. Pat. No. 5,166,328 does not disclose the use of indole-3-propionic acid in forming stable salts of SAMe, or a pharmaceutically acceptable salt thereof.

Furthermore, U.S. Pat. No. 2,969,353 discloses a method for the preparation of SAMe and a stable salt of SAMe but not the use of indole-3-propionic acid in forming a stable salt of SAMe, or a pharmaceutically acceptable salt thereof. U.S. Pat. No. 4,764,603 discloses the use of new salts of SAMe but does not disclose the use of indole-3-propionic acid in forming a stable salt of SAMe, or a pharmaceutically acceptable salt thereof. U.S. Pat. No. 5,073,546 discloses new salts of SAMe but does not disclose the use of indole-3-propionic acid in forming stable salts of SAMe, or a pharmaceutically acceptable salt thereof. U.S. Pat. No. 6,117,849 discloses the use of SAMe complexed with nucleosides as HIV inhibitors but does not disclose the use of indole-3-propionic acid in forming stable salts of SAMe, or a pharmaceutically acceptable salt thereof.

Indole-3-propionic Acid (IPA)

Indole-3-propionic acid (3-(3-Indolyl) propionic acid) (IPA) is a natural compound found in plants and animals, including humans. It has been found in mammalian plasma and cerebrospinal fluid, including human plasma and cerebrospinal fluid. Indole-3-propionic acid and SAMe are both available commercially.

IPA, while a naturally occurring compound found in mammalian plasma, including human plasma as a byproduct of gut microflora, can breakdown into degradation byproducts that may be potentially toxic. Potentially toxic byproducts can form via an oxidation reaction, especially in the presence of light.

The presence of such toxic byproducts can be ascertained by making an aqueous solution of IPA and observing the solution over time. Degradation is enhanced in light and at basic pH and the solution will develop a yellow color, or there will be an observed increased UV absorption at 420 nm. A yellow coloration of the solution could also be due to the formation of kynuric acid and, to differentiate kynuric acid from the potentially toxic degradation product, one can determine the absorption UV fluorescence peak of the toxic product, which has been reported at a slightly higher wavelength than 420 nm.

Compositions comprising IPA and SAMe, or a pharmaceutically acceptable salt thereof are disclosed in U.S. Published Patent Application Nos. 2010/0004191 and 2006/0127506. However, the compositions disclosed therein are not IPA salts of SAMe, or a pharmaceutically acceptable salt thereof. Furthermore, the compositions disclosed therein did not solve the problem of IPA degradation.

There is therefore a great need in the art for stable IPA salts of SAMe that not only offer superior stability of the SAMe molecule per se, but also offer few gastrointestinal side effects of the previously known SAMe salts and increased stability of IPA. There is also a need for methods directed to the therapeutic use of such salts to increase blood and other tissue and fluid levels of SAMe and to treat conditions which result from low blood and tissue levels of SAMe. There is also a need in the art for synthetic routes to make such stable IPA salts of SAMe and salts thereof. The present invention fulfills these needs and provides further related advantages.

SUMMARY OF THE INVENTION

The present invention is directed to stable indole-3-propionic acid (IPA) salts of S-adenosyl-L-methionine (SAMe), or a pharmaceutically acceptable salt thereof, pharmaceutical compositions comprising the salts, therapeutic methods for the use thereof and synthetic methods for the preparation of these IPA salts of SAMe, or a pharmaceutically acceptable salt thereof. These IPA salts of SAMe, or a pharmaceutically acceptable salt thereof, have utility in increasing methylation levels of DNA and RNA and blood and other tissue or fluid levels of SAMe in a mammal, preferably a human, as well as treating or preventing a wide variety of conditions associated with DNA hypomethylation, RNA hypomethylation, protein hypomethylation, lowered blood and tissue levels of SAMe.

Accordingly, in one aspect, this invention is directed to an indole-3-propionic acid salt of S-adenosyl-L-methionine, or a pharmaceutically acceptable salt thereof.

In another aspect, this invention is directed to an indole-3-propionic acid salt of S-adenosyl-L-methionine, or a pharmaceutically acceptable salt thereof, wherein the pharmaceutically acceptable salt of S-adenosyl-L-methionine is prepared from hydrochloric acid, sulphuric acid, phosphoric acid, phosphorous acid, disulphonic acid or 1,4 butanedisulphonic acid.

In another aspect, this invention is directed to an indole-3-propionic acid salt of S-adenosyl-L-methionine, or a pharmaceutically acceptable salt thereof, wherein the pharmaceutically acceptable salt of S-adenosyl-L-methionine is selected from S-adenosyl-L-methionine tosylate bisulfate, S-adenosyl-L-methionine p-toluenesulfonate, S-adenosyl-L-methionine bisulfate, S-adenosyl-L-methionine tri-p-toluenesulfonate, S-adenosyl-L-methionine di-p-toluenesulfonate, S-adenosyl-L-methionine disulfate, S-adenosyl-L-methionine chloride, S-adenosyl-L-methionine carbonate, S-adenosyl-L-methionine bicarbonate, S-adenosyl-L-methionine bromide, S-adenosyl-L-methionine iodide and S-adenosyl-L-methionine 1,4-butanedisulfonate.

In another aspect, this invention is directed to an indole-3-propionic acid salt of S-adenosyl-L-methionine, or a pharmaceutically acceptable salt thereof, wherein the pharmaceutically acceptable salt of S-adenosyl-L-methionine is S-adenosyl-L-methionine p-toluenesulfonate or S-adenosyl-L-methionine 1,4-butanedisulfonate.

In another aspect, this invention is directed to S-adenosyl-L-methionine p-toluenesulfonate indole-3-propionate salt or S-adenosyl-L-methionine 1,4-butanedisulfonate indole-3-propionate salt.

In another aspect, this invention is directed to a pharmaceutical composition comprising a pharmaceutically acceptable carrier and an effective amount of an indole-3-propionic acid salt of S-adenosyl-L-methionine, or a pharmaceutically acceptable salt thereof.

In another aspect, this invention is directed to a pharmaceutical composition comprising a pharmaceutically acceptable carrier, an effective amount of an indole-3-propionic acid salt of S-adenosyl-L-methionine, or a pharmaceutically acceptable salt thereof, and optionally an absorption enhancer.

In another aspect, this invention is directed to methods of treating a disease or disorder in a mammal alleviated by an increase in methylation levels of DNA and RNA in the mammal and/or by an increase in S-adenosyl-L-methionine levels in blood and other tissue of the mammal, wherein the method comprises administering to the mammal in need thereof an effective amount of an indole-3-propionic acid salt of S-adenosyl-L-methionine, or a pharmaceutically acceptable salt thereof, or an effective amount of a pharmaceutical composition comprising a pharmaceutically acceptable carrier, optionally an absorption enhancer and an effective amount of an indole-3-propionic acid salt of S-adenosyl-L-methionine, or a pharmaceutically acceptable salt thereof, wherein the disease or disorder in the mammal is selected from a mental or psychiatric disorder, a nervous system or neurological disease or disorder, conditions associated with injury to the central nervous system, a liver disease or disorder, a cancer, a joint disease or disorder, an inflammatory disease or disorder, an autoimmune disease or disorder, a degenerative disease or disorder, a soft-tissue disease or disorder, a pain disease or disorder, genetic disorders associate with hypo-methylation, a gastrointestinal disease or disorder, a cardiovascular disease or disorder, and a disorder induced in whole or in part by oxidative or free-radical damage, metabolic syndrome, type 1 and 2 diabetes and their complications.

In another aspect, this invention is directed to a process of preparing an indole-3-propionic acid salt of S-adenosyl-L-methionine, or a pharmaceutically acceptable salt thereof, wherein the method comprises treating a solution of S-adenosyl-L-methionine, or a pharmaceutically acceptable salt thereof, with an appropriate reagent under standard conditions with a solution of indole-3-propionic acid under standard conditions and isolating the indole-3-propionic salt from the reaction mixture by standard techniques.

Specific embodiments of these aspects of the invention are described in more detail below.

DETAILED DESCRIPTION OF THE INVENTION

Definitions

Unless defined otherwise in the specification, the following terms and phrases shall have the following meaning:

The term "SAMe" refers to S-adenosyl-L-methionine, as a racemic mixture of its diastereoisomers, as a non-racemic mixture of its diastereoisomers or as a substantially optically pure diastereoisomer. A non-racemic mixture includes mixtures where the ratio of the (S,S)S-adenosyl-L-methionine diastereoisomer to the (R,S)S-adenosyl-L-methionine diastereoisomer is about 1% to 99% or where the ratio is about 99% to 1%.

SAMe is commercially available using fermentation technologies that result in SAMe formulations varying between 60 and 80% purity (i.e., the final product contains 60-80% of the active diastereoisomer ((S,S)-SAMe) and 20-40% of the inactive diastereoisomer ((R,S)-SAMe) (Gross, A., Geresh, S., and Whitesides, Gm (1983) *Appl. Biochem. Biotech.* 8, 415). Enzymatic synthetic methodologies have been reported to yield the inactive isomer in concentrations exceeding 60% (Matos, J R, Rauschel F M, Wong, C H, "S-Adenosylmethionine: Studies on Chemical and Enzymatic Synthesis", *Biotechnology and Applied Biochemistry* 9, 39-52 (1987). U.S. Published Patent Application No. 2002/0188116 discloses methodology to synthesize SAMe but does not disclose any methodology to stabilize the molecule once it is synthesized. U.S. Published Patent Application No. 2002/0173012 also discloses a process for the preparation of a relatively purified biologically active diastereomer (S,S) SAMe (97%) but does not disclose the stabilization of the SAMe molecule by the formation of a IPA salt thereof.

The term "pharmaceutically acceptable salts" of SAMe includes, but is not limited to, pharmaceutically acceptable salts prepared from hydrochloric acid, sulphuric acid, phosphoric acid, phosphorous acid, sulphonic acid and 1,4 butanedisulphonic acid; and may include the following salts: SAMe tosylate bisulfate, SAMe-1,4-butanedisulfonate, SAMe sulfate, and SAMe tosylate.

Additionally, a pharmaceutically acceptable salt of SAMe may prepared from sulphonic acids selected from the group consisting of methanesulphonic acid, ethanesulphonic acid, 1-n-dodecanesulphonic acid, 1-n-octadecanesulphonic acid, 2-chloroethanesulphonic acid, 2-bromoethanesulphonic acid, 2-hydroxyethanesulphonic acid, 3-hydroxypropanesulphonic acid, d-,1-,d,-1-10-camphorsulphonic acid, d-,1-,d, 1-3-bromocamphor-10-sulphonic acid, cysteic acid, benzenesulphonic acid, p-chlorobenzenesulphonic acid, 2-mesitylbenzenesulphonic acid, 4-biphenylsulphonic acid, 1-naphthalenesulphonic acid, 2-naphthalenesulphonic acid, 5-sulphosalicylic acid, p-acetylbenzenesulphonic acid, 1,2-ethanedisulphonic acid, o-benzenedisulphonic and chondroitinesulphuric acids, and double salts of said acids with sulphuric acid.

A pharmaceutically acceptable salt of SAMe may be further selected from the group consisting of SAMe bisulfate, SAMe tri-p-toluenesulfonate, SAMe di-p-toluenesulfonate, SAMe disulfate, SAMe chloride, SAMe carbonate, SAMe bicarbonate, SAMe bromide, and SAMe iodide.

The IPA salts of SAMe, or a pharmaceutically acceptable salt thereof, of the invention comprise at least 0.01 to 1.0 mole of IPA to one mole of SAMe or a pharmaceutically acceptable salt thereof. In one embodiment, a IPA salt of SAMe, or a pharmaceutically acceptable salt thereof, of the invention comprises at least 0.01 to 1.0 mole of IPA to one mole of SAMe 1,4-butanedisulfonate salt. In another embodiment, a IPA salt of SAMe, or a pharmaceutically acceptable salt thereof, of the invention comprises at least 0.01 to 1.0 mole of IPA to one mole of SAMe p-toluenesulfonate salt. In another embodiment, a IPA salt of SAMe, or a pharmaceutically acceptable salt thereof, of the invention comprises at least 0.01 to 2.0 moles of IPA to one mole of SAMe (free base).

The term "IPA" refers to indole-3-propionic acid.

The term "treat" or "treatment" means that the symptoms associated with one or more conditions associated DNA hypomethylation, RNA hypomethylation, and protein hypomethylation are alleviated or reduced in severity or frequency and the term "prevent" means that subsequent occurrences of such symptoms are avoided or that the frequency between such occurrences is prolonged.

The term "conditions" includes diseases, injuries, disorders, indications and/or afflictions that are associated DNA hypomethylation, RNA hypomethylation, and protein hypomethylation.

As noted above, potential problems exist with IPA instability and the purity of IPA is not always assured and will contain some contaminants. In addition, IPA itself is poorly water soluble. In contrast, the IPA salt of SAMe of a salt thereof is highly water soluble. Degradation of IPA is thus prevented by the invention disclosed herein by making an IPA salt of SAMe or a pharmaceutically acceptable salt thereof.

The IPA salts of SAMe, or a pharmaceutically acceptable salt thereof, of the invention are more stable at room temperature over a longer period of time than previously known salts of SAMe. Furthermore, the IPA salts of SAMe, or a pharmaceutically acceptable salt thereof, of the invention do not cause gastrointestinal upset often associated with the previously known SAMe salts. In this regard, and in view of the well-known molecular instability of SAMe at room temperature over time, the IPA salts of SAMe or a salt thereof of the invention are able to withstand the conditions of room temperature over long periods of time. Such characteristic duplicates the shelf life conditions under which the IPA salts of SAMe, or a pharmaceutically acceptable salt thereof, of the invention would be stored.

Furthermore, the IPA salts of SAMe, or a pharmaceutically acceptable salt thereof, of the invention have additional advantages when compared to the previously known salts of SAMe, such as ease of manufacture and comfort of administration.

The IPA salts of SAMe, or a pharmaceutically acceptable salt thereof, of the invention therefore provide a more stable configuration for both SAMe and IPA, thereby essentially solving the main stability problems of each of these important biologically active molecules in one step. In particular, the IPA salts of SAMe, or pharmaceutically acceptable salt thereof, of the invention provide steric hindrance to the unstable SAMe molecule resulting in a much more stable molecule over time. Furthermore, the IPA salts of SAMe, or pharmaceutically acceptable salt thereof, of the invention render the IPA molecule incorporated therein water soluble at a very economical cost.

Utility, Administration and Pharmaceutical Compositions

The IPA salts of SAMe, or a pharmaceutically acceptable salt thereof, of the invention have significant utility over a wide range of disorders or conditions associated with DNA hypomethylation, RNA hypomethylation, lowered blood and tissue levels of SAMe.

Thus, in one embodiment, the IPA salts of SAMe, or pharmaceutically acceptable salt thereof, of the invention are administered to a mammal, preferably a human, in need thereof to increase SAMe levels. In another embodiment the IPA salts of SAMe, or pharmaceutically acceptable salt thereof, of the invention are administered to a mammal, preferably a human, in need thereof to prevent or treat a condition or disorder associated with or caused by DNA hypomethylation, RNA hypomethylation, lowered blood and tissue levels of SAMe or hypomethylation of certain promoter regions of genes whose expression one wishes to control or modulate. An example of this would be using the IPA salts of SAMe, or a pharmaceutically acceptable salt thereof, of the invention to control the hypomethylation of the LINE-1 or ALU elements of the genome to treat or prevent diseases associated with global DNA hypomethylation that occurs in aging diseases such as cancer, osteoarthritis, mild cognitive impairment, Alzheimer's disease and others.

A further embodiment provides a method of treating a disorder selected from the group consisting of aging, osteoarthritis, rheumatoid arthritis, fibromyalgia, menopause symptoms such as hot flashes, a psychiatric disorder, an inflammatory condition, a central nervous system (CNS) disorder, a pain disorder, a liver disorder, a neurological disorder, a gastrointestinal disorder, a cardiovascular disorder, a disorder induced in whole or in part by oxidative or free-radical damage, and a cancer, comprising administering to the patient in need thereof IPA salts of SAMe, or a pharmaceutically acceptable salt thereof, of the invention. In some embodiments, the disorder is a liver disorder selected from the group consisting of alcoholic liver disease, fatty liver disease and hepatitis. In some embodiments, the disorder is a gastrointestinal disorder such as inflammatory bowel disease (IBD), Crohn's disease or ulcerative colitis (UC).

In some embodiments, the disorder to be treated with IPA salts of SAMe, or a pharmaceutically acceptable salt thereof, of the invention is a psychiatric disorder selected from the group consisting of depressive disorders, eating disorders, bipolar disorder, abuse disorders, dependence disorders, Axis II disorders, psychosis and anxiety disorders. In some embodiments, the psychiatric disorder is an anxiety disorder selected from the group consisting of generalized anxiety disorder, post traumatic stress disorder, panic disorder and obsessive compulsive disorder. In some embodiments, the psychiatric disorder is a depressive disorder. In some embodiments, the depressive disorder is major depressive disorder, minor depression, brief recurrent depression, dysthymia or depression NOS.

In some embodiments, the psychiatric disorder to be treated with IPA salts of SAMe, or a pharmaceutically acceptable salt thereof, of the invention is an eating disorder selected from the group consisting of bulimia nervosa, anorexia nervosa, binge eating disorder, obesity, or eating disorder NOS. In some embodiments, the psychiatric disorder is bipolar disorder, an abuse disorder or a dependence disorder. In some embodiments, the psychiatric disorder includes abuse of, or dependence on, alcohol, cocaine, codeine, oxycodone, hydrocodone or other opiates.

In some embodiments, the psychiatric disorder to be treated with IPA salts of SAMe, or a pharmaceutically acceptable salt thereof, of the invention is an Axis II disorder selected from borderline personality disorder. In some embodiments, the disorder is a CNS disorder such as Parkinson's syndrome or Alzheimer's disease. In some embodiments, the disorder is an inflammatory disorder selected from the group comprising systemic lupus erythematosis, Reye's syndrome, rheumatic fever, allergic rhinitis, myasthenia gravis, temporal arteritis, vasculitis, psoriasis, atopic dermatitis, rosacea, eczema, alopecia universalis, scleroderma, pemphigus, contact dermatitis, ankylosing spondylitis, dermatomyositis, polymyositis, celiac sprue, Guillain-Barre syndrome, multi-infarct dementia, post cerebral vascular accident reperfusion damage, Addison's disease, Hashimoto's thyroiditis, asthma, upper respiratory inflammation symptoms, chronic bronchitis, atherosclerosis, pernicious anemia, autoimmune hepatitis, prostatitis, pelvic inflammatory disease, Goodpasture's syndrome, Wegener's granulomatosis, chronic nephritis, Sjogrens syndrome, or allergic conjuntivitis.

In some embodiments, the etiology of the disorder to be treated with IPA salts of SAMe, or a pharmaceutically acceptable salt thereof, of the invention may include oxidative or free-radical damage, and is selected from the group comprising chronic fatigue syndrome, temporal arteritis, vasculitis, multi-infarct dementia, chronic emphysema, or chronic nephritis. In some embodiments, the disorder is a cancer selected from the group consisting of cancers occurring in one or more of the liver, colon, rectum, ovaries, urethra, testicles, bladder, breast, stomach, esophagus, pancreas, head and neck, and adenocarcinomas, blood cancer, skin cancer and any metastatic cancers. In addition, the IPA salts of SAMe, or a pharmaceutically acceptable salt thereof, of the invention are useful for preventing or treatment chemo as well as radiation resistant cancer cells.

This invention further provides a method for inhibiting the abnormal growth of cells, including transformed cells, by administering an effective amount of a IPA salt of SAMe, or a pharmaceutically acceptable salt thereof, of the invention. Abnormal growth of cells refers to cell growth independent of normal regulatory mechanisms (e.g., loss of contact inhibition). This includes the inhibition of tumor growth both directly by causing growth arrest, terminal differentiation and/or apoptosis of cancer cells, and indirectly, by inhibiting neovascularization of tumors.

This invention also provides a method for inhibiting tumor growth by administering an effective amount of an IPA salt of SAMe, or a pharmaceutically acceptable salt thereof, of the invention, to a subject, e.g. a mammal (preferably a human) in need of such treatment. In particular, this invention provides a method for inhibiting the growth of tumors by the administration of an effective amount of a IPA salt of SAMe, or a pharmaceutically acceptable salt thereof, of the invention.

Examples of tumors which may be inhibited include, but are not limited to, lung cancer (e.g., adenocarcinoma and including non-small cell lung cancer), pancreatic cancers (e.g., pancreatic carcinoma such as, for example exocrine pancreatic carcinoma), colon cancers (e.g., colorectal carcinomas, such as, for example, colon adenocarcinoma and colon adenoma), prostate cancer including the advanced disease, hematopoietic tumors of lymphoid lineage (e.g., acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g., fibrosarcomas and rhabdomyosarcomas), melanomas, teratocarcinomas, neuroblastomas, gliomas, benign tumor of the skin (e.g., keratoacanthomas), breast carcinoma (e.g., advanced breast cancer), kidney carcinoma, ovary carcinoma, bladder carcinoma and epidermal carcinoma.

The IPA salts of SAMe, or a pharmaceutically acceptable salt thereof, of the invention may be used for other therapeutic purposes, for example: a) the sensitization of tumors to radiotherapy by administering the new salts according to the invention before, during or after irradiation of the tumor for treating cancer; b) treating arthropathies and osteopathological conditions such as rheumatoid arthritis, osteoarthritis, juvenile arthritis, gout, polyarthritis, psoriatic arthritis, ankylosing spondylitis and systemic lupus erythematosus; c) inhibiting smooth muscle cell proliferation including vascular proliferative disorders, atherosclerosis and restenosis; d) treating inflammatory conditions and dermal conditions such as ulcerative colitis, Crohn's disease, allergic rhinitis, graft vs. host disease, conjunctivitis, asthma, ARDS, Behcets disease, transplant rejection, urticaria, allergic dermatitis, alopecia greata, scleroderma, exanthema, eczema, dermatomyositis, acne, diabetes, metabolic syndrome, systemic lupus erythematosis, Kawasaki's disease, multiple sclerosis, emphysema, cystic fibrosis and chronic bronchitis; e) treating endometriosis, uterine fibroids, dysfunctional uterine bleeding and endometrial hyperplasia; f) treating ocular vascularisation including vasculopathy affecting retinal and choroidal vessels; g) treating a cardiac dysfunction; h) inhibiting immunosuppressive conditions such as the treatment of HIV infections; i) treating renal dysfunction; j) suppressing endocrine disorders; k) inhibiting dysfunction of gluconeogenesis; l) treating a neuropathology for example Parkinson's disease or a neuropathology that results in a cognitive disorder, for example, Alzheimer's disease or polyglutamine related neuronal diseases; m) inhibiting a neuromuscular pathology, for example, amylotrophic lateral sclerosis; n) treating spinal muscular atrophy; o) treating other pathologic conditions amenable to treatment by potentiating expression of a gene; p) enhancing gene therapy.

Administration of the IPA salts of SAMe or pharmaceutically acceptable salt thereof of the invention to a mammal, preferably a human, in need thereof may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

In a preferred embodiment, the IPA salts of SAMe or pharmaceutically acceptable salt thereof of the invention is administered to a mammal, preferably a human, as a pharmaceutical, prophylactic or cosmetic composition containing at least one substantially optically pure diastereomeric form of a IPA salt of SAMe or pharmaceutically acceptable salt thereof of the invention or a non-racemic mixture of a IPA salt of (S,S)—S-adenosyl-L-methionine and (R,S)—S-adenosyl-L-methionine, or a pharmaceutically acceptable salt thereof, in combination with at least one pharmaceutically, prophylactically or cosmetically acceptable carrier or diluent and one absorption enhancer.

Administration may be accomplished by systemic or topical application, with the preferred mode dependent upon the type and location of the conditions to be treated. Frequency of administration may vary, and is typically accomplished by daily administration. Typical oral dosages for the IPA salts of SAMe, or a pharmaceutically acceptable salt thereof, of the invention for the treatment of the conditions listed above lie in the range of from 100 mg to 1600 mg or greater per day per patient given in divided doses. Intravenous dosages for SAMe or pharmaceutically salts thereof have already been established and oral dosages are currently being established for indole-3-propionic acid.

For prophylactic or therapeutic applications, the dose administered to a mammal, preferably a human, in the context of the present invention, should be sufficient to effect a beneficial response in the mammal over time (i.e., an effective amount). This amount, which will be apparent to the skilled artisan, depends on the species, age, and weight of the individual; the type of disease to be treated; in some cases the sex of the individual; and other factors which are routinely taken into consideration when treating individuals at risk for, or having, a disease.

Topical administration of the IPA salts of SAMe, or a pharmaceutically acceptable salt thereof, of the invention may include the use of transdermal patches, ointments, lotions, creams, gels, drops, suppositories, sprays, liquids and powders.

In some embodiments, in addition to the administration of IPA salts of SAMe, or a pharmaceutically acceptable salt thereof, of the invention, one or more additional pharmaceutical agents selected from vitamin B12 (B12), folate (folic acid or a biologically acceptable salt thereof), or both may be given simultaneously to the mammal, preferably a human, in need thereof.

Pharmaceutical compositions comprising a IPA salt of SAMe or a pharmaceutically acceptable salt there of the invention and a pharmaceutically acceptable carrier may be prepared by methods known to one skilled in the art and used in the administration of the IPA salts of SAMe, or a pharmaceutically acceptable salt thereof, of the invention. Conventional pharmaceutically acceptable carriers are well known in the art.

For example, a pharmaceutical composition of the invention may be prepared by combining a IPA salt of SAMe, or a pharmaceutically acceptable salt thereof, of the invention in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the IPA salts of SAMe, or a pharmaceutically acceptable salt thereof, of the invention in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

In pharmaceutical compositions of the invention suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount of a IPA salt of SAMe or a pharmaceutically acceptable salts thereof of the invention. In general it is contemplated that a therapeutically effective amount of a IPA salt of SAMe or a pharmaceutically acceptable salts thereof of the invention would be from 0.005 mg/kg to 100 mg/kg body weight, and in particular from 0.5 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

Pharmaceutical compositions for oral administration of a IPA salt of SAMe, or a pharmaceutically acceptable salt thereof, of the invention may also include thickeners, flavoring agents, diluents, emulsifiers, dispersing aids, binders or absorption enhancers.

The absorption enhancers may be from about 0.0025% to about 100% of the weight of the active ingredient in the pharmaceutical compositions of this invention. However, the best concentration of absorption enhancers relative to the weight of the IPA salt of SAMe or pharmaceutically acceptable salt thereof of the invention is that concentration or amount of absorption enhancers that result in the maximum increase in absorption of the IPA salt of SAMe or pharmaceutically acceptable salt thereof of the invention. That amount or concentration is readily ascertained by the pharmacokinetic analyses as described in the known pharmaceutical art.

Typical absorption enhancers are chosen from the group consisting of chitosan, chitosan derivatives, such as but not limited to, chitosan chloride, trimethyl chitosan, trimethyl chitosan homopolymer, poly(acrylic acid), cytochalasin D; caprate, spermine, taurocholate (including sodium and other salt forms) and other bile acids and/or their salts (such as cholic acid, sodium cholate or potassium cholate), as well as more recently identified agents which include peptides derived from zonula occludens toxin or *Clostridium perfringens* enterotoxin, saturated and/or unsaturated fatty acids or their corresponding carboxylate salts (e.g., C6-C24 fatty acids, or carboxylate salts thereof, especially C8-C22 fatty acids, or carboxylate salts thereof, C10-C20 fatty acids or carboxylate salts thereof, C6-, C7-, C8-, C9-, C10-, C11-, C12-, C13-, C14-, C15-, C16-, C17-, C18-, C19-, C20-, C21-, C22-fatty acids or carboxylate salts thereof), saturated and unsaturated sulfonic acids and sulfonate salts thereof (e.g., C6-C24 sulfonic acids or sulfonate salts, especially C8-C22 sulfonic acids or sulfonate salts, C10-C20 sulfonic acids or sulfonate salts, C8-, C9-, C10-, C11-, C12-, C13-, C14-, C15-, C16-, C17-, C18-, C19-, C20-, C21-, C22- sulfonic acids or sulfonate salts); zwitterionic surfactants (e.g., 3-(N,N-dimethylpalmitylammonio) propanesulfonate, decyldimethyl ammonio propane sulfonate, myistyldimethyl ammonio propoane sulfonate, cocamidopropyl hydroxysultaine (ChemBetaine® CAS), oleyl betaine (ChemBetaine® Oleyl), or palmitoyl carnitine chloride); fatty amines (e.g., C6-C24 fatty amines, especially C8-C22 fatty amines, C10-C20 fatty amines, C6-, C7-, C8-, C9-, C10-, C11-, C12-, C13-, C14-, C15-, C16-, C17-, C18-, C19-, C20-, C21-, C22-fatty amines), as well as other organic acids (e.g., tartaric acid) and cyclodextrins (e.g., alpha-cyclodextrin, beta-cyclodextrin, or gamma-cyclodextrin) and labrasol.

Exemplary fatty acids that may be used as absorption enhancers include hexanoic, heptanoic, capric, lauric acid, myristic acid, palmitic acid, stearic acid, arachidic acid, myristoleic acid, palmitoleic acid, sapienic acid, oleic acid, linoleic acid, a-linolenic acid, arachidonic acid, eicosapentaenoic acid, erucic acid, docosahexaenoic acid.

Exemplary carboxylate salts that may be used as absorption enhancers include sodium or potassium captrate, caprylate, laurate, myristate, palmitate, stearate, arachidate, myristoleate, palmitoleate, sapienate, oleate, linoleate, a-linolenate, arachidonate, eicosapentaenoate, erucate, docosahexaenoate. Specific carboxylate salts include sodium caprate, sodium caprylate, and sodium laurate. Specific fatty amines that may be used include lauryl amine (N-dodecylamine), decylamine, nonylamine, octylamine, heptylamine or hexylamine.

Exemplary sulfonic acids that may be used as absorption enhancers include octane sulfonic acid, decane sulfonic acid (e.g. sodium 1-decanesulfonate), dodecane sulfonic acid, tetradecane sulfonic acid, hexadecane sulfonic acid, octadecane sulfonic acid, eicosane sulfonic acid, docosane sulfonic acid or tetracosane sulfonic acid. Specific sulfonic acids that may be mentioned include dioctyl sodium sulfosuccinate.

In some embodiments, the absorption enhancers used in the pharmaceutical compositions of the invention can be a zwitterionic surfactant such as an acyl carnitine. In some embodiments, said acyl carnitine is a palmitoyl carnitine, lauroyl carnitine, stearoyl carnitine, myristoyl carnitine, decanoyl carnitine, or a salt thereof. In some embodiments, said zwitterionic surfactant is a sulfobetaine. In some embodiments, said sulfobetaine is sulfobetaine-10, sulfobetaine-12, sulfobetaine-14, sulfobetaine-16, or sulfobetaine-18.

The invention additionally relates also to pharmaceutical compositions comprising a physiologically acceptable dosage of a IPA salt of SAMe or pharmaceutically acceptable salt thereof of the invention and at least one absorption enhancer. In preferred embodiments, said absorption enhancer is co-formulated with the physiologically acceptable dosage of a IPA salt of SAMe or pharmaceutically acceptable salt thereof of the invention.

Preparation of IPA Salts of SAMe, or Pharmaceutically Acceptable Salts Thereof

In general, the IPA salts of SAMe, or pharmaceutically acceptable salts thereof, of the invention are prepared by 1) adding indole-3-propionic acid (or a salt thereof) to water; 2) adding S-adenosyl-L-methionine, or pharmaceutically acceptable salt thereof, to the indole-3-propionic acid solution at a pH from 1.0 to 6.9; 3) stirring the reaction mixture; 4) isolating the product from the reaction mixture; and, optionally, 5) lyophilizing the product to produce a stable powder.

The final lyophilization is carried out by the usual methods, to give an IPA salt of 100% purity. Any drying method may be used to obtain a powder, for example, spray drying, but the preferred method is lyophilization.

Stability of the IPA salt can be assessed by the method disclosed in Bottiglieri, T. (1990), *Biomed Chromatogr,* 4(6):239-41.

The following examples illustrate synthetic processes by which IPA salts of SAMe, or pharmaceutically acceptable salts, thereof of the invention may be made. Known salts of indole-3-propionic acid may be used in the following synthesis since IPA itself is poorly water-soluble. These examples are given to illustrate the present invention, but not by way of limitation. Accordingly, the scope of this invention should be determined not by the embodiments illustrated, but rather by the appended claims and their legal equivalents.

SYNTHETIC EXAMPLE 1

S-Adenosyl-L-methionine p-toluenesulfonate indole-3-propionate

A. To a stirred solution of S-adenosyl-L-methionine p-toluenesulfonate salt (100 mg, 0.128 mmol, Sigma Aldrich lot#021M5158V) in HPLC grade water (2.5 mL) was added barium carbonate (125 mg, 0.63 mmol) and stirred for 5 minutes and left standing for another 5 minutes. The S-adenosyl-L-methionine free base generated was filtered from the precipitated p-toluensulfonate salt directly into a vial containing indole-3-propionic acid (IPA) (67 mg, 0.354 mmol, Sigma Aldrich lot #1431484V), and vigorously stirred for 1 hr. The resulting suspension was lyophilized to yield a white solid. The resulting solid was washed with ethyl acetate (3×3 mL) and filtered. The filtered solid was dried to yield 109 mg of S-adenosyl-L-methionine p-toluenesulfonate indole-3-propionate salt; $^1$H NMR (300 MHz, $D_2O$) δ 8.14 (s), 7.6 (d), 7.34 (d), 7.2 (d) 6.98-7.09 (m) 5.97 (s) 4.80-4.83 (s) 4.2-4.6 (m), 3.2-3.91 (m), 2.7-3.0 (m), 2.45 (t), 2.1-2.3 (s).

B. The ethyl acetate washes above were combined and concentrated under reduced pressure to yield 55 mg of indole-3-propionic acid as a white solid; $^1$H NMR (300

MHz, DMSO-d$_6$) δ 7.6 (d, 1H), 7.34 (d, 1H), 6.98-7.09 (m, 3H), 2.9-3.0 (m, 2H), 2.65-2.35 (m, 3H).

SYNTHETIC EXAMPLE 2

S-Adenosyl-L-methionine 1,4-butanedisulfonate indole-3-propionate

A solution of S-adenosyl-L-methionine 1,4 butanedisulfonate (4.10 g, 6.67 mmol, Sigma Aldrich lot#021M5158V) in HPLC grade water (20 mL) was cooled to 0° C. and the pH of the solution was measured (pH 1.6) and adjusted to pH 7 by slow addition of 10% sodium hydroxide at 0-5° C. A solution of indole-3-propionic acid (5.50 g, 26.7 mmol, Sigma Aldrich lot #1431484V) in methanol was added and the reaction mixture was diluted with methanol to make it a uniform solution with a pH of around 5.3. The solution was stirred for thirty minutes and concentrated under reduced pressure to remove the methanol. The residual aqueous solution was lyophilized to remove water. The dry powder thus obtained was suspended in methanol and stirred for 10 minutes to remove excess indole-3-propionic acid. The salt was removed by filtration and washed with methanol to obtain 4.0 grams of S-adenosyl-L-methionine 1,4-butandisulfonate indole-3-propionate salt; $^1$H NMR (300 MHz, D$_2$O) δ 8.14 (d), 7.54 (d), 7.34 (d), 6.98-7.09 (m), 5.97 (d), 4.80-4.83 (t), 4.42-4.48 (m), 3.2-3.91 (m), 2.80-2.89 (m), 2.20-2.23 (m), 1.70-1.75 (m). Analysis of the product by thin layer chromatography showed no presence of free indole-3-propionic acid; analysis by NMR showed incorporation of 19.4% of indole-3-propionic acid.

UV Analysis of the Product of Synthetic Example 1 and Synthetic Example 2

Figure 1:
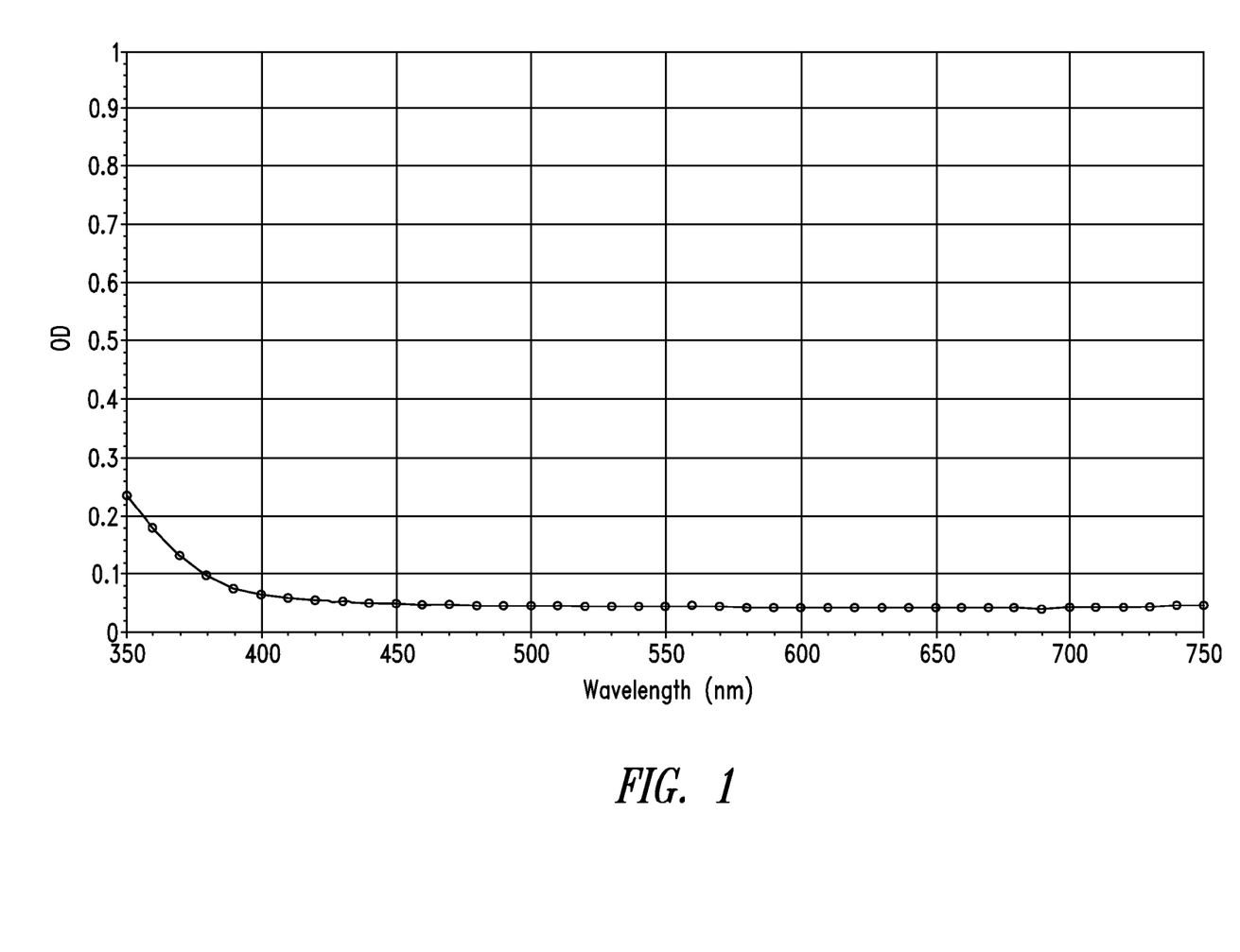
FIG. 1 is the UV absorption spectrum of the product of Synthetic Example 1.
Figure 2:
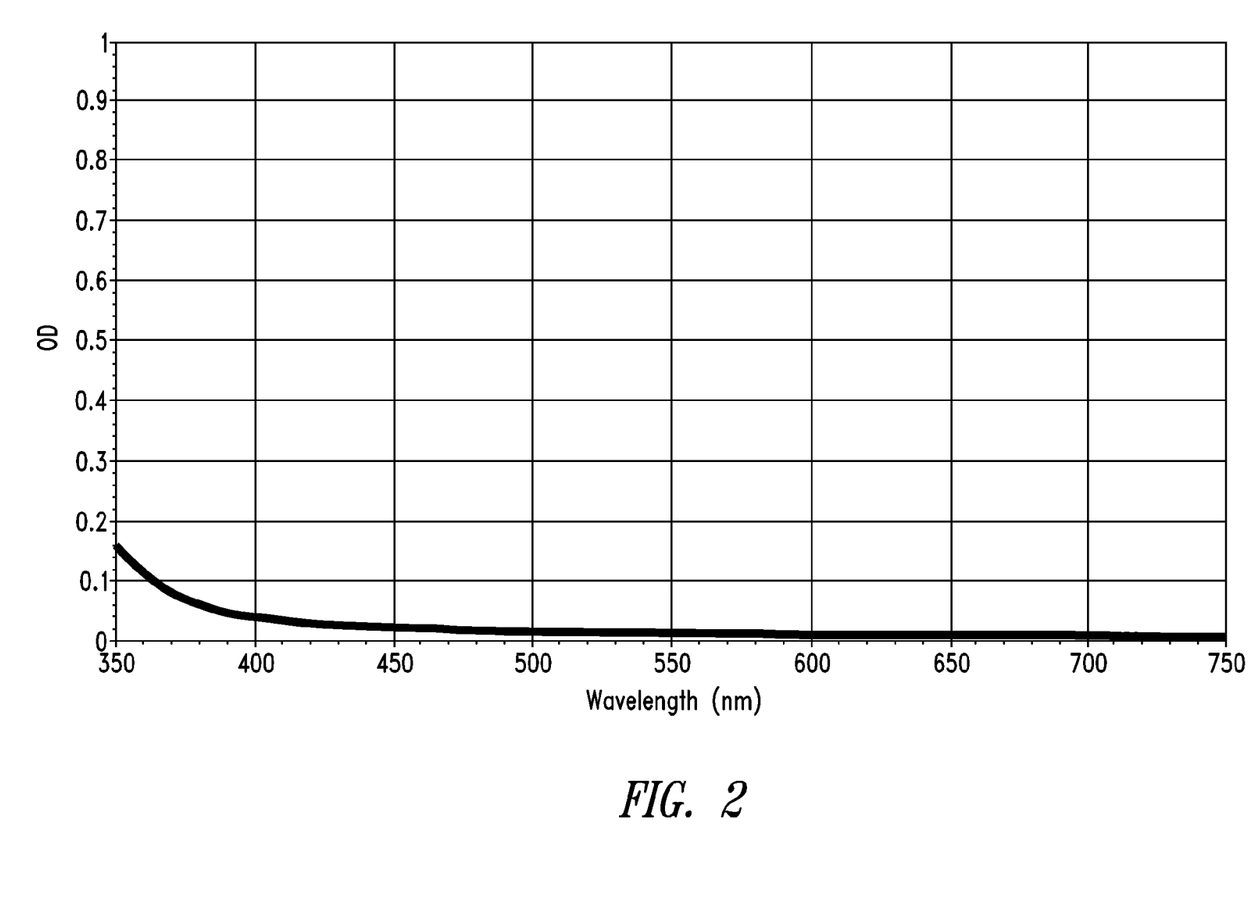
FIG. 2 is the UV absorption spectrum of the product of Synthetic Example 1. obtained eight months after the initial UV analysis of the product as shown in FIG. 1.
Figure 3:
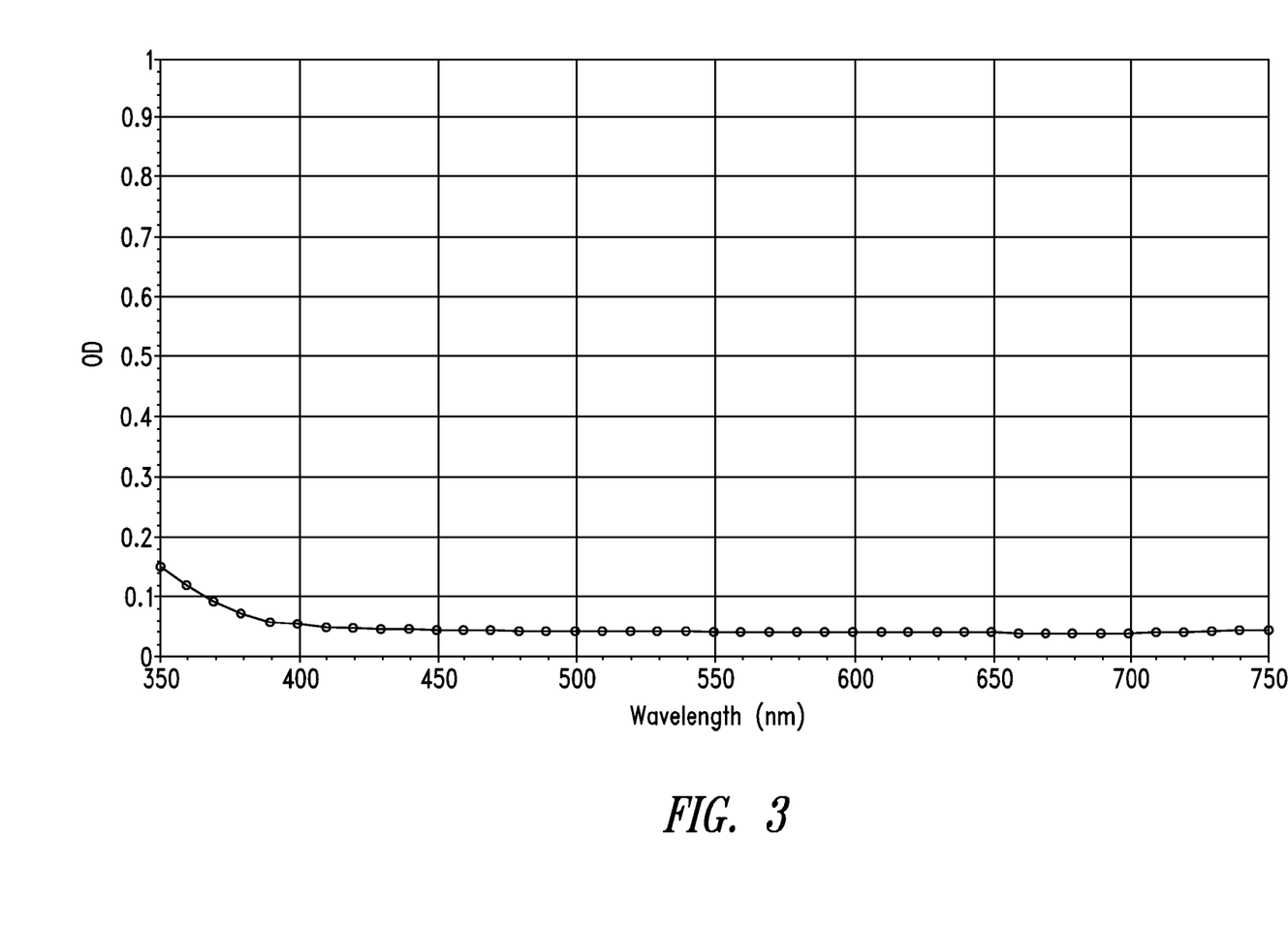
FIG. 3 is the UV absorption spectrum of the product of Synthetic Example 2.
Figure 5:
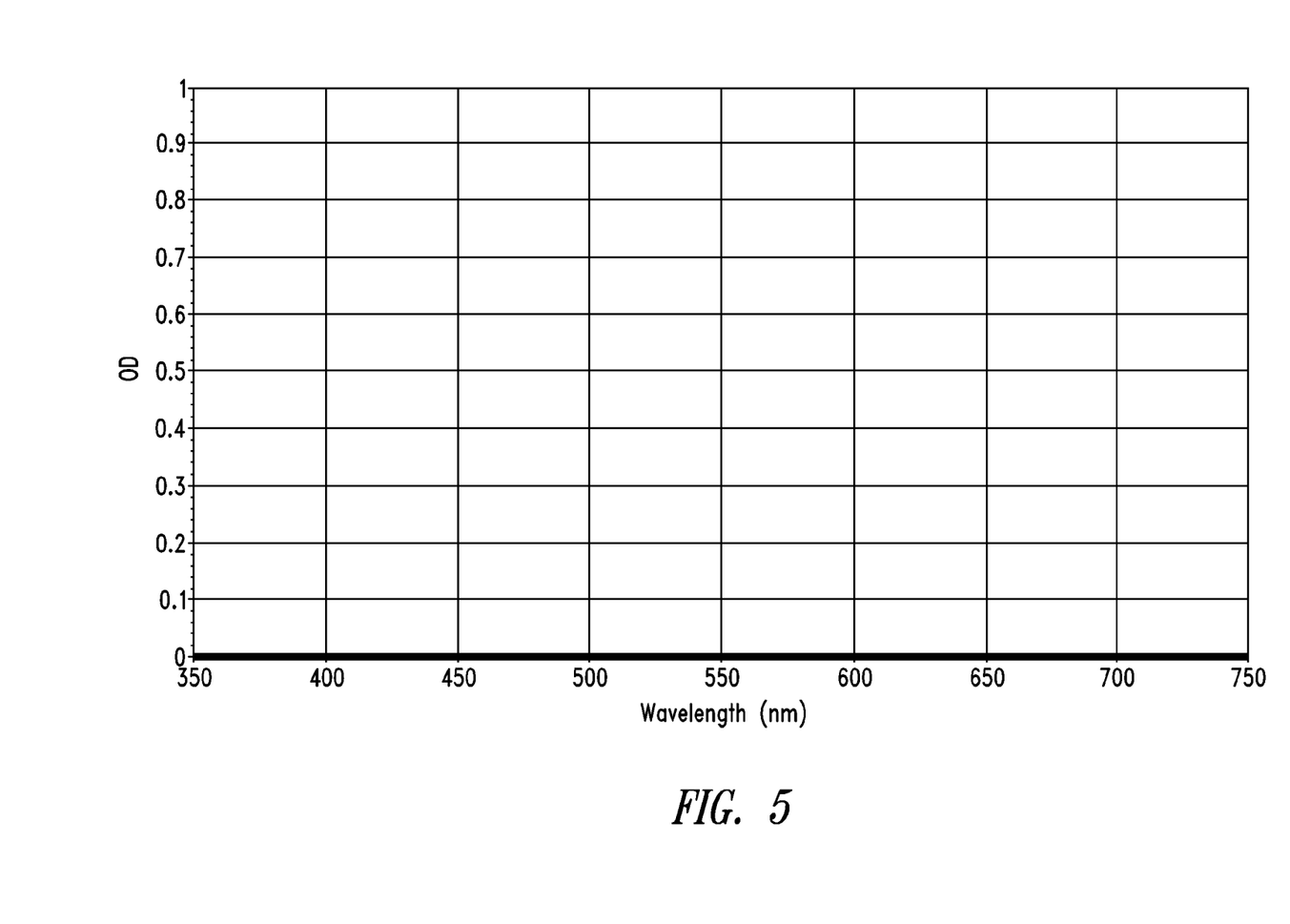
FIG. 5 is the UV absorption spectrum of a blank sample obtained at the same time as the UV absorption spectra of FIGS. 1 and 3 were obtained.

Ultraviolet-visible light absorption spectra were obtained for the product of Synthetic Example 1 and the product of Synthetic Example 2 (see FIG. 1 and FIG. 2, respectively). An ultraviolet-visible light absorption spectrum was also obtained at the same time for a blank sample (see FIG. 5) for control purposes.

Figure 4:
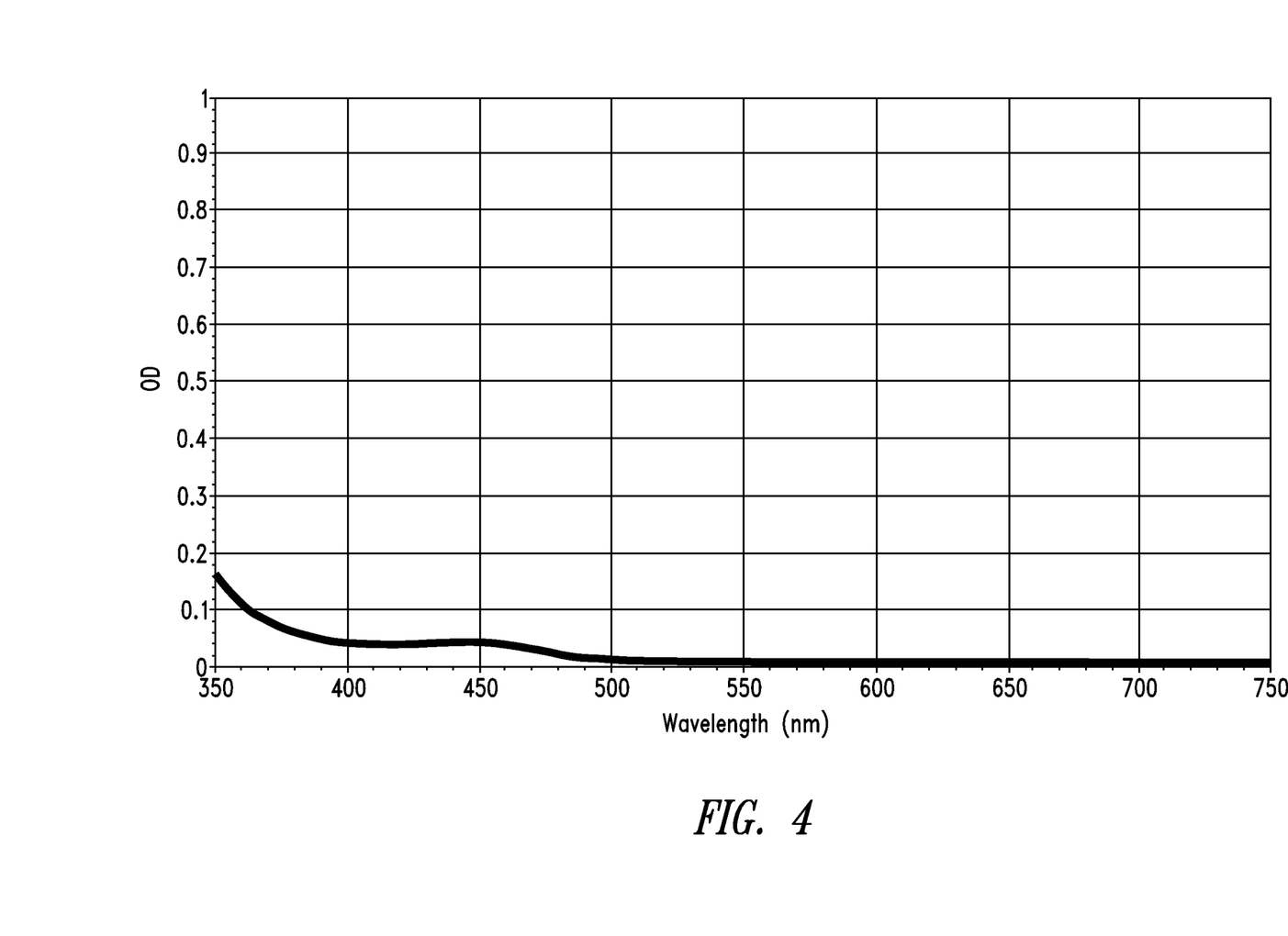
FIG. 4 is the UV absorption spectrum of the product of Synthetic Example 2 obtained eight months after the initial UV analysis of the product as shown in FIG. 3.
Figure 6:
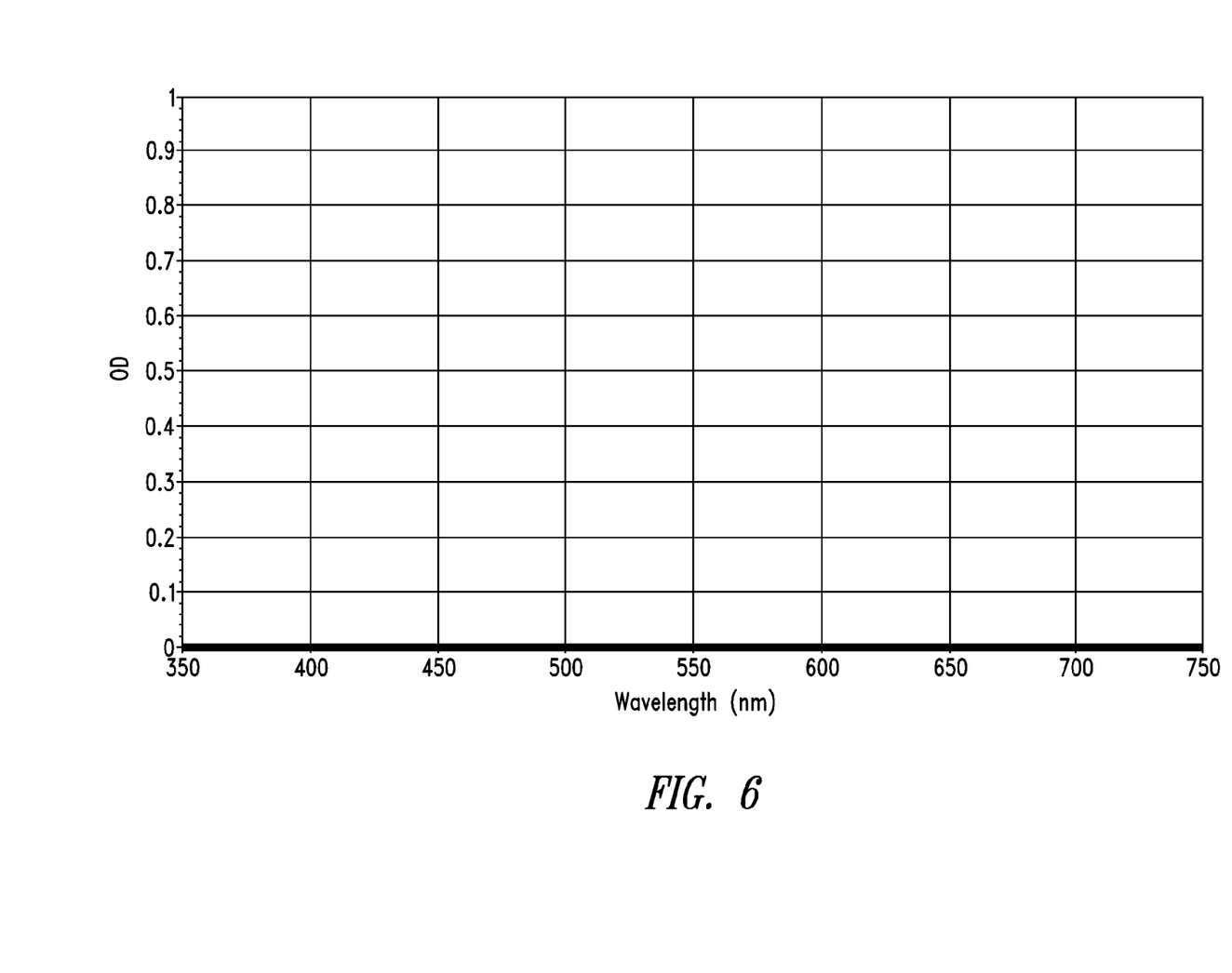
FIG. 6 is the UV absorption spectrum of a blank sample obtained at the same time as the UV absorption spectra of FIGS. 2 and 4 were obtained.

The product of Synthetic Example 1 and the product of Synthetic Example 2 were then stored for eight months at room temperature, after which ultraviolet-visible light absorption spectra were obtained for the stored products (see FIG. 2 and FIG. 4). An ultraviolet-visible light absorption spectrum was also obtained at the same time for a blank sample (see FIG. 6) for control purposes.

No SAMe degradation products were detected by HPLC or by the UV absorption spectra, thus showing that the SAMe molecule remained stable for 8 months at room temperature. This is in stark contrast to the unstable nature of, for example, previously known salts of SAMe, such as the tosylate or 1,4-butanedisulfonate salts, the stability of which can be determined in the same manner as described herein. Furthermore, no maximum absorption peaks at 420 nm were noted in any of the UV absorption spectras obtained, indicating the absence of the toxic degradation products for the incorporated IPA.

BIOLOGICAL EXAMPLE 1

In Vitro Permeability Assay

The following in vitro permeability assay was conducted to determine the efficacy of certain absorption enhancers in increasing the permeability of a IPA salt of SAMe, or a pharmaceutically acceptable salt thereof, of the invention. See Stewart, B H, et al. (1995) "Comparison of intestinal permeabilities determined in multiple in vitro and in situ models: Relationship to absorption in humans," *Pharm. Res.* 12:693.

Test Compound

The test compound was the IPA salt of SAMe 1,4-butanedisulfonate (the product of Synthetic Example 2) (SAMeIPA). The concentration of the test compound used in the assay was 2 mM.

Absorption Enhancers

The absorption enhancers tested with the test compound in this assay were trimethyl chitosan homopolymer (HPTMC), trimethyl chitosan (TMC) and chitosan HCl (chitosan).

Test Formulations

The following formulations were tested:
1. SAMeIPA (with no absorption enhancer added)
2. SAMeIPA and 0.025% chitosan
3. SAMeIPA and 0.25% chitosan
4. SAMeIPA and 2.5% TMC
5. SAMeIPA and 2.5% HPTMC Controls Ranitidine was use for the low permeability control and warfarin was used for the high permeability control.

Analytical Methods

The signal was optimized for each test formulation by ESI positive or negative ionization mode. An MS2 scan or a SIM scan was used to optimize the fragmenter voltage and a product ion analysis was used to identify the best fragment for analysis, and the collision energy was optimized using a product ion or MRM scan. An ionization ranking was assigned indicating the formulation's ease of ionization.

Samples were analyzed by LC/MS/MS using an Agilent 6410 mass spectrometer coupled with an Agilent 1200 HPLC and a CTC PAL chilled autosampler, all controlled by MassHunter software (Agilent). After separation on a C18 reverse phase HPLC column (Agilent, Waters, or equivalent) using an acetonitrile-water gradient system, peaks were analyzed by mass spectrometry (MS) using ESI ionization in MRM mode.

The permeability of SAMe and IPA were measured independently.

Experimental Conditions

Caco-2 cells grown in tissue culture flasks were trypsinized, suspended in medium, and the suspensions were applied to wells of a collagen-coated BioCoat Cell Environment in 96-well format. The cells are allowed to grow and differentiate for three weeks, feeding at 2-day intervals.

For Apical to Basolateral (A->B) permeability, the test formulation was added to the apical (A) side and amount of permeation is determined on the basolateral (B) side; for Basolateral to Apical (B>A) permeability, the test formulation was added to the B side and the amount of permeation was determined on the A side. The A-side buffer contained 100 μM Lucifer yellow dye, in Transport Buffer (1.98 g/L glucose in 10 mM HEPES, 1× Hank's Balanced Salt Solution) pH 6.5, and the B-side buffer was Transport Buffer, pH 7.4. CaCo-2 cells were incubated with these buffers for 2 hours, and the receiver side buffer was removed for analysis by LC/MS/MS.

To verify the Caco-2 cell monolayers were properly formed, aliquots of the cell buffers were analyzed by fluorescence to determine the transport of the impermeable dye Lucifer Yellow.

Data was expressed as apparent permeability ($P_{app}$).

Results

The results of the assay are shown below in Table 1:

TABLE 1

| Test Formulation | Analyte | mean A->B $P_{app}$ | Comments |
|---|---|---|---|
| Ranitidine | Ranitidine | 0.3 | low permeability control |
| Warfarin | Warfarin | 40.1 | high permeability control |
| SAMeIPA | SAMe | 0.20 | |
| SAMeIPA and 0.025% chitosan | SAMe | 0.98 | 4.9 fold increase |
| SAMeIPA and 0.25% chitosan | SAMe | 1.9 | 9.5 fold increase |
| SAMeIPA and 2.5% TMC | SAMe | 0.93 | 4.7 fold increase |
| SAMeIPA and 2.5% HPTMC | SAMe | 7.5 | 37.5 fold increase |
| SAMeIPA | IPA | 0.20 | |
| SAMeIPA and 0.025% chitosan | IPA | 0.98 | 4.9 fold increase |
| SAMeIPA and 0.25% chitosan | IPA | 1.9 | 9.5 fold increase |
| SAMeIPA and 2.5% TMC | IPA | 0.93 | 4.7 fold increase |
| SAMeIPA and 2.5% HPTMC | IPA | 7.5 | 37.5 fold increase |

Discussion

The Caco-2 cell line is derived from a human colorectal carcinoma and is widely used for in vitro cell culture models for the study of gastrointestinal drug absorption. In these models, pure cell lines are grown on a semi-permeable membrane. Drug formulations are placed on the apical or basolateral side of the cell monolayer and transport is determined via measurement of drug concentrations on the other side of the membrane.

As an example, the effect of the absorption enhancers (and specifically tight junction opening agents such as chitosan, chitosan chloride, trimethyl chitosan and trimethyl chitosan homopolymer) on Caco-2 permeability of S-adenosyl-L-methionine 1,4-butanedisulfonate indole-3-propionate salt is compared to absorption of S-adenosyl-L-methionine 1,4-butanedisulfonate indole-3-propionate salt without any absorption enhancers added. Wafarin is a high permeability marker and was used as a positive control for a readily absorbed molecule.

The results above in Table 1 show that the absorption of S-adenosyl-L-methionine is low for the S-adenosyl-L-methionine 1,4-butanedisulfonate indole-3-propionate salt without any absorption enhancers added, as evidenced by a low apparent permeability coefficient.

The measured permeability value of the S-adenosyl-L-methionine 1,4-butanedisulfonate indole-3-propionate salt was much lower than that measured with the high permeability marker, warfarin. The different absorption enhancers show different permeability enhancing profiles as shown by the different fold increases in S-adenosyl-L-methionine permeability with the greatest increase in permeability shown using trimethyl chitosan homopolymer as the absorption enhancer (37.5 fold increase.)

Indole-3-propionic acid is also poorly absorbed and thus the effects of the different absorption enhancers were also studied in this assay. However, in contrast to the significant increases in permeability of S-adenosyl-L-methionine, indole-3-propionic acid showed some slight increase in permeability with the various absorption enhancers.

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. An indole-3-propionic acid salt of S-adenosyl-L-methionine, or a pharmaceutically acceptable salt thereof.

2. The indole-3-propionic acid salt of claim 1 wherein the pharmaceutically acceptable salt of S-adenosyl-L-methionine is prepared from hydrochloric acid, sulphuric acid, phosphoric acid, phosphorous acid, disulphonic acid or 1,4 butanedisulphonic acid.

3. The indole-3-propionic acid salt of claim 1 wherein the pharmaceutically acceptable salt of S-adenosyl-L-methionine is selected from S-adenosyl-L- methionine tosylate bisulfate, S-adenosyl-L-methionine p-toluenesulfonate, S-adenosyl-L- methionine bisulfate, S-adenosyl-L-methionine tri-p-toluenesulfonate, S-adenosyl-L-methionine di-p-toluenesulfonate, S-adenosyl-L-methionine disulfate, S-adenosyl-L-methionine chloride, S- adenosyl-L-methionine carbonate, S-adenosyl-L-methionine bicarbonate, S-adenosyl-L-methionine bromide, S-adenosyl-L-methionine iodide and S-adenosyl-L-methionine 1,4-butanedisulfonate.

4. The indole-3-propionic acid salt of claim 1 wherein the pharmaceutically acceptable salt of S-adenosyl-L-methionine is S-adenosyl-L-methionine p-toluenesulfonate or S-adenosyl-L-methionine 1,4-butanedisulfonate.

5. The indole-3-propionic acid salt of claim 1 which is selected from S-adenosyl-L-methionine p-toluenesulfonate indole-3-propionate salt or S- adenosyl-L-methionine 1,4-butanedisulfonate indole-3-propionate salt.

6. A pharmaceutical composition comprising a pharmaceutically acceptable carrier and an effective amount of an indole-3-propionic acid salt of S-adenosyl-L-methionine, or a pharmaceutically acceptable salt thereof.

7. The pharmaceutical composition of claim 6 further comprising one or more absorption enhancers.

8. A method of treating a disease or disorder in a mammal alleviated by an increase in methylation levels of DNA and RNA in the mammal and/or by an increase in S-adenosyl-L-methionine levels in blood and other tissue of the mammal, wherein the method comprises administering to the mammal in need thereof an effective amount of an indole-3-propionic acid salt of S-adenosyl-L-methionine, or a pharmaceutically acceptable salt thereof, or an effective amount of a pharmaceutical composition comprising a pharmaceutically acceptable carrier and an effective amount of an indole-3-propionic acid salt of S-adenosyl-L-methionine or a pharmaceutically acceptable salt thereof, and wherein the disease or disorder in the mammal is selected from a mental or psychiatric disorder, a nervous system or neurological disease or disorder, conditions associated with injury to the central nervous system, a liver disease or disorder, a cancer , a joint disease or disorder, an inflammatory disease or disorder, an autoimmune disease or disorder, a degenerative disease or disorder, a soft-tissue disease or disorder, a pain disease or disorder, genetic disorders associate with hypo-methylation, a gastrointestinal disease or disorder, a cardiovascular disease or disorder, and a disorder induced in whole or in part by oxidative or free-radical damage, metabolic syndrome, type 1 and 2 diabetes and their complications.

9. A process of preparing an indole-3-propionic acid salt of S-adenosyl-L-methionine, or a pharmaceutically acceptable salt thereof, wherein the method comprises treating a solution of S-adenosyl-L-methionine, or a pharmaceutically acceptable salt thereof, with an appropriate reagent under standard conditions with a solution of indole-3-propionic acid under standard conditions and isolating the indole-3-propionic salt from the reaction mixture by standard techniques.

10. The pharmaceutical composition of claim 7, wherein the one or more absorption enhancers are selected from the group consisting of chitosan, chitosan chloride, trimethyl chitosan, and trimethyl chitosan homopolymer.

* * * * *